(12) United States Patent
Leivseth et al.

(10) Patent No.: US 6,905,471 B2
(45) Date of Patent: Jun. 14, 2005

(54) METHOD AND DEVICE FOR TRAINING PELVIC FLOOR MUSCLES

(75) Inventors: Gunnar Leivseth, Trondheim (NO); Ole Olsen, Langesund (NO)

(73) Assignee: Innovative Development & Marketing, Trondheim (NO)

( * ) Notice: Subject to any disclaimer, the term of this patent is extended or adjusted under 35 U.S.C. 154(b) by 83 days.

(21) Appl. No.: 10/153,692

(22) Filed: May 24, 2002

(65) Prior Publication Data

US 2003/0220589 A1 Nov. 27, 2003

Related U.S. Application Data (63) Continuation of application No. PCT/SE00/02320, filed on Nov. 24, 2000.

(51) Int. Cl.[7] .......................... A61B 5/103; A61B 5/117
(52) U.S. Cl. ...................................... 600/591
(58) Field of Search .......................... 600/30, 591, 38; 73/379.08, 379.01; 128/DIG. 25; 482/111, 112; 601/45; 607/138

(56) References Cited

U.S. PATENT DOCUMENTS

| | | | |
|---|---|---|---|
| 5,483,832 A | * | 1/1996 | Pauser et al. ............ 73/379.08 |
| 5,674,238 A | | 10/1997 | Sample et al. |
| 5,733,230 A | * | 3/1998 | Sawchuck et al. .......... 482/111 |
| 5,782,745 A | * | 7/1998 | Benderev ...................... 600/30 |
| 6,741,895 B1 | * | 5/2004 | Gafni et al. ................ 607/138 |

FOREIGN PATENT DOCUMENTS

| | | |
|---|---|---|
| DE | 19753030 A1 | 6/1999 |
| WO | WO 99/26699 | 6/1999 |

* cited by examiner

*Primary Examiner*—Max F. Hindenburg
*Assistant Examiner*—Brian Szmal (57) ABSTRACT

A method and device for training pelvic floor muscles in order to treat or prevent urinary or fecal incontinence. The device comprises a probe having a pressure sensor and a vibrator, and a microprocessor connected with the sensor and the vibrator. Initially, the probe is inserted into a person's vagina or rectum and the highest force that can be applied by the person contracting the pelvic muscles is ascertained and registered. The contraction of the pelvic floor muscles is repeated at intervals, and the force applied by pelvic floor muscles at each contraction is ascertained and compared with the registered highest value. The vibrator is activated at each contraction of the floor muscles only if the force has a predetermined relationship to the registered value, and only for a predetermined period as long as the predetermined relationship is maintained.

19 Claims, 6 Drawing Sheets

METHOD AND DEVICE FOR TRAINING PELVIC FLOOR MUSCLES

This applications is a continuation of PCT/SE00/02320 filed Nov. 24, 2000.

BACKGROUND OF THE INVENTION

1. Field of the Invention

The invention relates to method and device for training pelvic floor muscles in order to cure or prevent urinary or fecal incontinence.

More particularly, this invention pertains to novel method and device (perineometer) which can be used by medical professionals for diagnostic purposes and by woman or men at home or in non-medical environment for pelvic floor muscle exercise comprising contraction of the muscles, in order to maintain the muscle strength after childbirth so as to prevent urinary incontinence (prophylactic effect) or to provide increased muscle strength of a person who already suffers of urinary or focal incontinence in an effort to cure the incontinence (therapeutic effect).

2. Description of Related Art

The prevalence of urinary incontinence, especially among postmenopausal women, is estimated to be within 22–42% of the population. Up to 50 to 70% of the institutionalized female elderly are affected. The most common form is stress urinary incontinence. Incontinence may result from a sudden raise in bladder pressure that exceeds urethral resistance. This rise may occur under conditions such as coughing, sneezing, lifting, or some other form of activity.

Female continence is maintained through the integrated normal function of pelvic floor muscles, fascial structures, nerves, supporting ligaments, and the vagina. Different theories, e.g. Shafik's 'common sphinkter' concept, Delancey's 'hammock' hypothesis, and Petros'& Ulmsten's 'integral theory', are used to explain how this integrated system is mandatory for continence. The important role of normal functioning of pelvic floor tissues is common to these theories.

Continence might be maintained despite defective function in one or more of the structures involved in the continence mechanism through increased efficacy in the unaffected tissues. In some cases therefore, stress urinary incontinence might be the result of failed compensatory effects by the other tissues, e.g. reduced muscular force, reduced muscular endurance, or reduced active and passive tone of the pelvic floor muscles. Different studies have shown the importance of pelvic floor muscles in the maintenance of urinary continence. Appropriate pelvic muscle exercises have been found to strengthen the pelvic floor structures, which increases the capacity of the structures to maintain the continence mechanism, and thus reduces or eliminates urinary incontinence.

Among medical professionals, e.g. obstetricians, gynecologists, geriatricians, urotherapists, physiotherapists, and nurses, there is a general agreement that three different treatments exist for urinary incontinence. These include: pelvic exercises, medication, and surgery.

A H Kegel was among the first to document the positive effects of isometric exercises on the pelvic floor musculature. Kegel recommended the use of perineometers for biofeedback in pelvic muscle training. Simultaneous training with biofeedback has proven successful and has been corroborated by several investigators.

The Kegel perineometer suffered from several drawbacks. There was no provision in Kegel's vaginal probe for establishing a predetermined base-line pressure in the vaginal probe when the patient's vaginal muscles were relaxed. The manometer in the Kegel perineometer was difficult to read, both because the numbers and graduations were necessarily small to accommodate the full range of possible pressures on the dial face, and because small fluctuations in the strength of the patient's vaginal contractions could give rise to rapid and erratic movements of the manometer's indicating needle. The Kegel perineometer had no provisions for assisting the patient in timing or regulating the duration of her vaginal contractions, or for calculating the average strength thereof.

A variant of Kegel's device, disclosed in U.S. Pat. No. 2,507,858 issued May 16, 1950, comprises an inflatable member which can be inserted into vagina to indicate pneumatically the change in pressure on an associated dial gauge. U.S. Pat. No. 2,541,520 issued Feb. 13, 1951 to A. H. Kegel, illustrates a similar type of apparatus except that the applicator is inflatable via a pneumatic bulb.

Another variant of Kegel's perineometer was developed by Wilfred Lynch Associates of Racine, Wis. This device, called a pelvic floor exerciser, included a vaginal probe consisting of a sponge covered by a balloon. The probe is contracted prior to insertion by evacuating most of the air from the probe by means of a hand operated syringe. The patient then removes the syringe, caps off the opening of the probe, inserts the probe in her vagina, allows the probe to expand by uncapping the opening of the probe, and connects the opening of the probe to a flexible tube, which in turn is connected to a ball-in-tube meter apparently measuring the rate of change of the pressure in the probe.

When the pelvic floor exerciser is in use, the patient must keep one hand on the probe to retain it in her vaginal, and must hold the meter with her other hand so that the bell-in-tube portion is perpendicular to the ground. She then contracts her vaginal muscles and watches the ball as it rises and instantaneously falls again in response to the initial rate of change of her vaginal contraction. During the exercise the patient must perceive and record the maximum height reached by the ball in the tube. The difficulties with the Lynch exerciser are numerous and obvious. It is not an improvement of the Kegel's perineometer except for the fact that the vaginal probe is reduced in size prior to insertion.

Another variant of Kegel's perineometer has been developed recently by M. Dougherty at the College of Nursing of the University of Florida at Gainsville. This device involves an elaborate and expensive compressible intravaginal balloon device that is custom made to fit the interior of a particular patient's vagina. The device is then pneumatically connected to a pressure measuring device, the output of which is recorded on a strip chart. The Dougherty device has no apparent advantages over the original Kegel perineometer, except for the developer's contention that the device will not inadvertently slip out of the patients vagina. However, the device has many disadvantages, including that it is extremely expensive, requires a separate custom-fitted appliance for each patient, utilizes complex scientific instrumentation, and can only be used under the supervision of a skilled attendant.

Numerous types of perineometer-like devices are also described in the patent literature. For example, U.S. Pat. No. 3,598,106 issued Aug. 10, 1971 to E. Buning, describes a noninflatable liquid-filled pressure indicating vaginal exerciser utilizing a conventional fluid pressure measuring device. U.S. Pat. No. 3,640,284 issued Feb. 8, 1972 to P. A. Delangis, describes an apparatus which measures vaginal pressure by means of a cylindrical condom holder filled with water, and a manometer. U.S. Pat. No. 3,726,273 issued Apr. 10, 1973 to N. S. Cole, discloses a vaginal exercising device consisting of an inflatable bulb having only expansion capability. Vaginal pressure is indicated by a conventional pneumatic pressure indicator. U.S. Pat. No. 3,752,150 issued Aug. 14., 1973 to J. P. Harris, discloses a device for exercising vaginal muscles using a liquid-filled pressurized insert wherein the pressure caused by muscular contraction is indicated on a conventional liquid pressure measuring device. U.S. Pat. No. 3,926,178 issued Dec. 16, 1975 to A. N. Feldzarnen, includes a device for exercising sphincter muscles, including vaginal muscles, utilizing a noninflatable insertable probe having two helical tubes. Readout of the pressure sensed by the probe may be effected by means of a conventional Bourdon tube, a liquid level pressure sensor, tubes filled with colored liquid, or a conventional pressure gauge. U.S. Pat. No. 4,050,449 issued Sep. 27, 1977 to F. S. Castellana et al., describes an air inflatable balloon-like insertable member including a collar to hold the inflatable member in place. Pressure is measured by means of a conventional dial pressure gauge. U.S. Pat. No. 4,085,985 issued Sep. 20, 1977 to H. A. Sasse, describes an air or liquid filled elongated tube probe which is directly connected to a pressure indicating gauge. U.S. Pat. No. 4,167,338 issued Sep. 18, 1979 to H. Remih, discloses a circumferentially expandable insertable body and a conventional air actuated mechanical indicator. Alternatively, an electronic display for digitally providing a pressure indication may be utilized. U.S. Pat. No. 4,216,783 issued Aug. 12, 1980 to H. Kaiser et al., shows an insertable probe whereby vaginal pressure may be measured by a conventional air pressure gauge in connection with biofeedback to increase the degree and strength of control exercised over the vaginal muscles. U.S. Pat. No. 4,476,880 issued Oct. 16, 1984 to D. A. Giem et al., discloses an air pressure operated tubular membrane wherein air pressure is converted to an electrical signal by means of a sensor. By specifically disclosed electronic circuitry, a visual display of the vaginal pressure may be obtained. U.S. Pat. No. 4,653,514 issued Mar. 31, 1987 and U.S. Pat. No. 4,768,522 issued Sep. 6, 1988 to S. W. Shapiro, describes insertable members which are partially deflated by means of a vacuum before insertion into the vagina. U.S. Pat. No. 5,674,238 issued Oct. 7, 1997 to S. B. Sample et al., describes an insertable air filled probe whose interior pressure may be varied by vaginal contractions. The perineometer includes a control module which indicates alternating periods of exercise and rest so that the patient may contract the muscles according to a predetermined length of time separated by periods of rest. The controller also includes means for indicating the difference between the probe interior pressure and a predetermined pressure during the period of exercise, as well as means for indicating the difference between the average pressure of the probe interior during a preceding exercise period and a predetermined pressure during a period of rest. U.S. Pat. No. 5,733,230 issued Mar. 31, 1998 to D. J. Sawchuck et al., describes an insertable air filled probe connected to a pneumatic pressure generator supported by a microprocessor unit.

The above mentioned pressure sensors have some common major drawbacks: Balloons sense pressure changes without the possibility to sense from which direction the increase in pressure occurs. This means that an increase in intra-abdominal pressure or increased activity of other pelvic or hip muscles may give rise to an increased pressure reading without activity in the pelvic floor musculature. To reduce these errors, a simultaneous evaluation/examination of the movement of the pelvic floor by means of manual palpation or visual observation is necessary in order to get subjective information about the activity of the pelvic floor. In addition, since the changes in the diameter of the balloon cannot be measured during a test, nor the changes in physical characteristics, it is not possible reliably to calculate the forces developed in the pelvic floor by means of these techniques. Recent studies have shown that the force developed in the pelvic floor musculature increases as the length of these muscles increases. This implies that different sizes of the perineometers, e.g. different pressures within the balloons, is an important confounding variable which makes it difficult to compare the readings from time to time within each subject. In addition, a comparison between different groups of subjects seems impossible.

A very different approach to measuring the contractile strength of the vaginal musculature involves electromyography. In this approach a set of electrodes is placed in physical contact with the interior walls of the patient's vagina. The electric potential differences among the probes are then measured by an electrometer, and from these measurements the degree of vaginal muscle contraction is inferred. Devices utilizing this approach are also called vaginal myographs.

Several vaginal myographs are marketed by Biotechnologies Inc. of Strafford, Pa. All myographs utilize a dumbbell-shaped solid vaginal probe which is made of hard dental acrylic, and which has three silver pads embedded around the contracted central portion of the probe. The probe is inserted into the patient's vagina, and is then connected by an electric cable to an assembly of amplifiers, integrators, computers, video displays, printers, recorders, telephone modems, quentized lighted bar displays, and other complex and expensive monitoring devices. These vaginal myographs suffer from a wide range of inherent problems. They are extremely expensive and most of the devices can be operated only by skilled health professionals after extensive specialized training.

There is no guarantee that these vaginal myographs measure the strength of contraction by the vaginal musculature. The level of electrical activity measured by these devices is determined by several variables, including the number of motor units firing, the rate of firing, the proximity of the motor units to the electrode, and the chemical characteristics of the vaginal fluid that forms the interface between the electrodes and the vaginal walls. These variables can give misleading variations in readings from one person to the next. The response of a vaginal myograph can also be affected by the contractions of muscles proximate to but distinct from those surrounding the vagina, such as the adductors or other hip muscles. Because the electrical signals picked up by the probe are at the microvolt level, vaginal myographs are extremely sensitive to electromagnetic interference. In addition, great measurement errors may occur when the pelvic floor tissue, or vaginal tissue, moves relative to the inserted myograph. Due to these movements an artificial increase in myographic activity arises with no relation to increased electrical activity of the examined tissue.

DE-A1-197 53 030 describes a probe to be inserted into a person's vagina or rectum and having a sensor for dynamically ascertaining the force applied by contraction of the pelvic floor muscles. The probe can be used by a physician in order to get information on the force that can be mobilised by contraction of the pelvic floor muscles by guidance of which a suitable treatment of the incontinence will be decided; surgery should not be resorted to if there is a possibility to improve the muscle strength e.g. by muscle exercise. The probe can also be used by the person at home in order to check the progress of improvement achieved by muscle exercise.

The therapeutic effect of vibratory stimulation on the human body has been well documented. Vibration at low frequencies applied to tissue increases blood circulation due to the increase in capillary dilation. The increased blood flow increases the consumption of oxygen and nutrients by muscles and improves the regeneration process. The result is an improved muscular tone, elasticity and contractile capacity.

U.S. Pat. No. 5,782,745 issued Jul. 21, 1998 to T. V. Benderev describes a device and method for assessment and treatment of urinary and fecal incontinence wherein a probe to be inserted into the vagina or the rectum is provided with a vibrator to provide vibratory stimulation to the vaginal or anal wall and/or adjacent muscles to facilitate strengthening of the pelvic floor muscles. The vibrator may be operated on a timed cycle.

BRIEF SUMMARY OF THE INVENTION

The primary object of the invention is to render exercise for strengthening the pelvic floor muscles more effective and to keep the exercise under control in an effort to improve the result obtained. This is achieved by providing a method for training pelvic floor muscles in order to cure or prevent urinary or fecal incontinence comprising the steps of inserting a probe with vibrator and force sensor into a person's vagina or rectum, ascertaining initially the highest value of the force that can be applied by the person at contraction of the pelvic floor muscles with the vibrator operating or not, registering said value, repeating the contraction of the pelvic floor muscles at intervals, ascertaining the force applied by the pelvic floor muscles at each contraction, comparing said force with said registered highest value, activating the vibrator if by comparison the force applied by the person at each contraction of the pelvic floor muscles has a predetermined relationship to said registered highest value, and maintaining the vibrator activated for a predetermined period as long as the predetermined relationship is maintained.

Thus, if the contraction force is in a predetermined relationship to the registered value, e.g. if it amounts to about 80% of said value, the exercise performed by repeatedly contracting the pelvic floor muscles will be supplemented by vibratory influence on the pelvic floor muscles. Then, the vibration will be maintained for a predetermined period.

The invention also provides a device for training pelvic floor muscles in order to cure or prevent urinary or fecal incontinence comprising a probe to be inserted into vagina or rectum, at least one sensor in the probe for ascertaining dynamically force transferred to the probe by the pelvic floor muscles, a vibrator in the probe, and a computer operatively connected with the sensor and the vibrator for energising the vibrator only at a value of the force as ascertained by the sensor, which is related to a predetermined value of said force.

In a preferred embodiment the probe comprises a first and a second element mutually spaced by an axial gap therebetween, a single sensor located in said first element for converting a force applied to said sensor into an electric output signal, and a lever system in said second element for transferring to the sensor from axially spaced positions of the probe dynamically passive and active forces induced by the pelvic floor muscles and acting on said first and second elements over said gap in the transverse direction of the probe when inserted in the vagina or rectum, and for applying said force to the sensor.

Further details of the invention are defined in the independent claims.

BRIEF DESCRIPTION OF THE DRAWINGS

The accompanying drawings disclose illustrative embodiments of the device of the invention, and the method of the invention will be described with reference to these embodiments.

In the drawings

DETAILED DESCRIPTION OF THE INVENTION

The embodiments described below are intended for use by health professionals in diagnosing urinary incontinence of woman and testing the strength of the pelvic floor muscles, and at home by the woman in order to conduct pelvic muscle training under domestic conditions and to asses the result thereof without direct medical supervision. However, the invention is not limited to such use; the probe can be adapted for insertion into rectum for diagnosing and curing fecal incontinence of woman and men. Thus, the size of the probe must be dimensioned with due consideration of the intended use of the probe in vagina or rectum.

Figure 1:
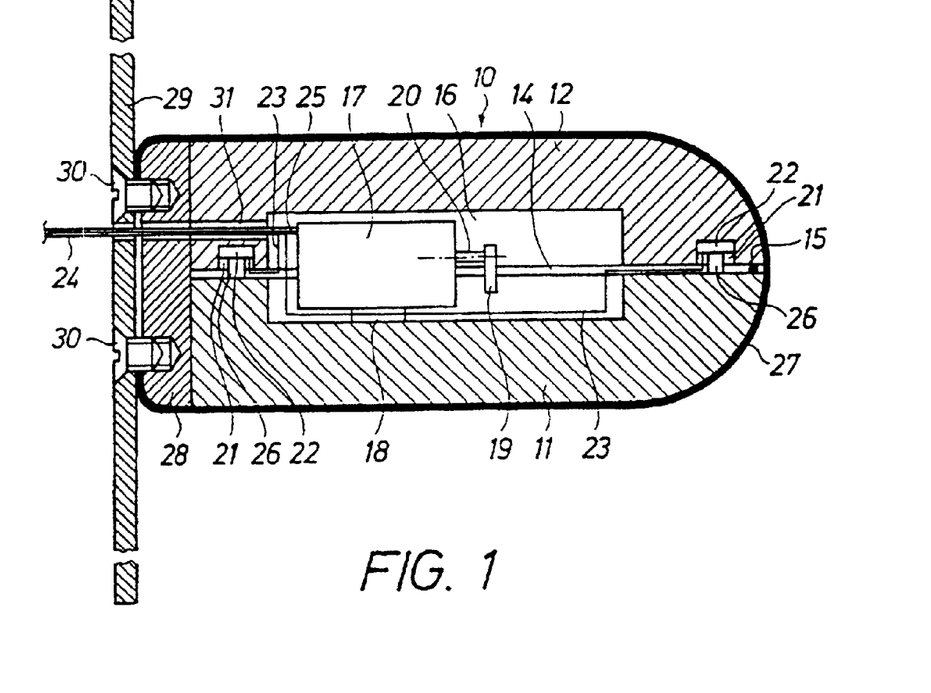
FIG. 1 is an axial cross sectional view of a first embodiment of the probe forming part of the device of the invention.
Figure 2:
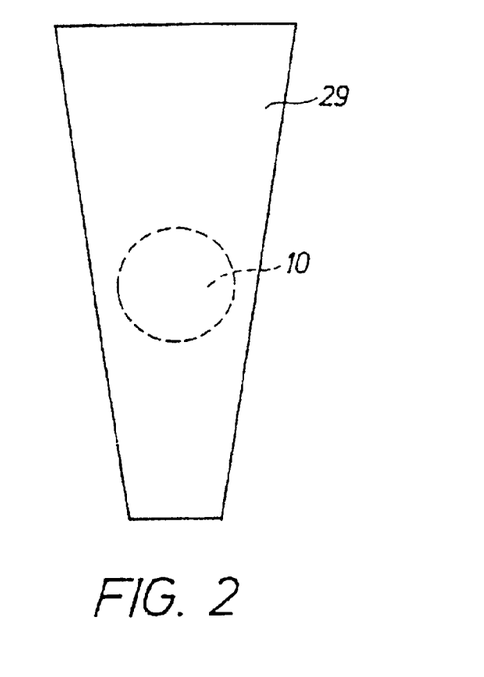
FIG. 2 is an end view on a reduced scale of the probe in FIG. 1.

Referring to FIGS. 1 and 2 the probe 10 disclosed therein as an illustrative embodiment is intended to be inserted into the vagina and is of cylindrical shape with a hemispherical end forming the insert or distal end of the probe. The probe can have another round shape, and it is not necessary that it is of unitary cross sectional shape but the shape disclosed herein has proven to be anatomically optimal. The probe comprises two halves 11 and 12 having flat surfaces facing each other in a central axial plane of the probe, a gap 14 of the order of 1 mm being left between the two halves and being maintained therebetween as will be described below. The two halves are articulately interconnected at 15 and should be made of a substantially rigid material, e.g. plastic material.

The two halves form together a cavity 16, and a vibrator received therein comprises an electric micro motor 17 connected to half 11 of the probe at 18, and an unbalanced weight 19 mounted on a drive shaft 20 of the motor. The motor can have a drive shaft projecting at each end of the motor, the projecting ends of the shaft having each an unbalanced weight, and the motor and vibrator can also be built together to form an integrated unit. Half 12 forms two recesses 21 located each near one end of the probe and opening into the flat surface of half 12, and in each of these recesses there is received a force sensor 22. A suitable sensor is a force sensitive resistor from International Electronics and Engineering, Findel, Luxembourg, which has the shape of a thin sandwich structure comprising interdigitating electrodes between carrier sheets. These sensors are available at a low price, are small and require a minimum of space, and the accuracy thereof is sufficient for the purposes of the invention. Electrical wires 23 are connected to the sensors and are extended to a cable 24 which also contains wires 25 for the supply of electric power to motor 17. A switch should be provided allowing the motor to be switched on and off manually. Pins 26 formed by or mounted on half 11 project from the flat surface thereof and engage each one of the sensors 22.

A condom 27 of latex or similar elastic material is stretched over the probe and is clamped between an end disk 28 abutting the end surface of the probe, and a plate 29 tightened against disk 28 by means of screws 30 screwed into threaded blind holes in the disk 28. The plate tapers from an upper end to a lower end thereof. The disk 28 is held against the end surface of the probe by the stretched condom, which keeps halves 11 and 12 together with pins 26 abutting sensors 22. The cable 24 is passed through a passage 31 extending from cavity 16 through the upper half 12 of the probe, the disk 28 and the plate 29 to an outside location.

Figure 3:
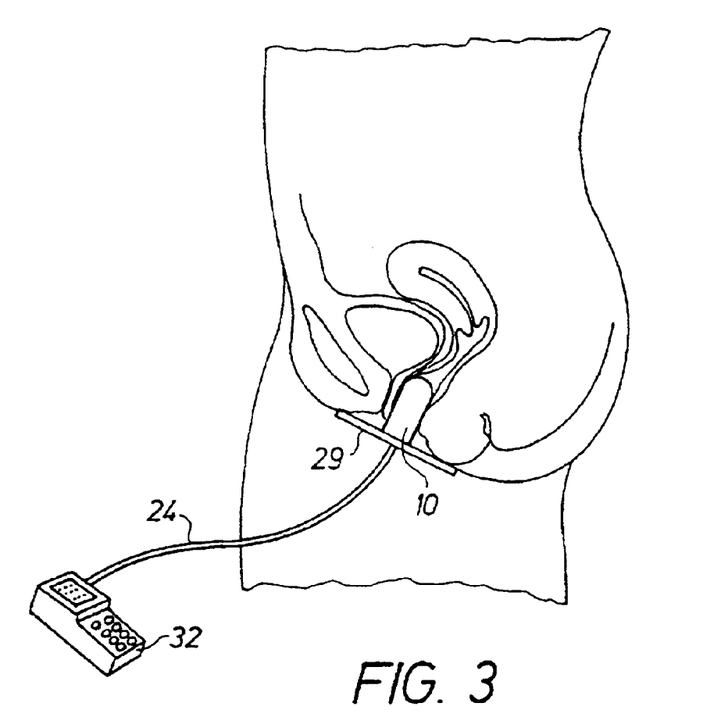
FIG. 3 is a fragmentary vertical cross sectional view of the human female body showing the device of the invention applied for exercise of the pelvic floor muscles.

With reference to FIG. 3 the probe 10 is inserted into a woman's vagina. The plate 29 at the outer or proximal end of the probe extends upwards and downwards to form a support plate which is engaged with the body at the opening of the vagina as disclosed in FIG. 2. The cable 24 is connected to a hand held battery operated electronic processing unit 32. As illustrated in FIG. 3 this unit comprises a microprocessor 33 including interfaces for the motor 17 and the sensors 22, a memory 34 for data storage, a timer circuit 35, and a controller 36 for setting the timer circuit. The unit also includes a battery 37. The unit is connected by the cable 24 to the motor 17 for the supply of electric power to the motor when the vibrator is to be activated.

When applying the method of the invention the probe disclosed in FIGS. 1 and 2 is introduced into a person's vagina as shown in FIG. 3, in order to cure or prevent female urinary incontinence. The probe is connected by the cable 24 to the unit 32. Initially the person by contracting the pelvic floor muscles applies the largest possible force that she is able to accomplish. During this step the vibrator can be switched off but preferably is operating. A signal representing the force applied is transmitted to the unit 32 at 38 to be stored in the memory 34, which can be effected by connecting the pressure sensitive probe directly to the unit over an interface or by reading the force on an indicator connected to the probe and then supplying the value of the force to the memory by means of a keyboard included in or connected to the unit. The unit can also have facilities for storing personal data, general set-up data, and time data, and a display for reading the stored data as well as an interface for connection to a PC.

Figure 4:
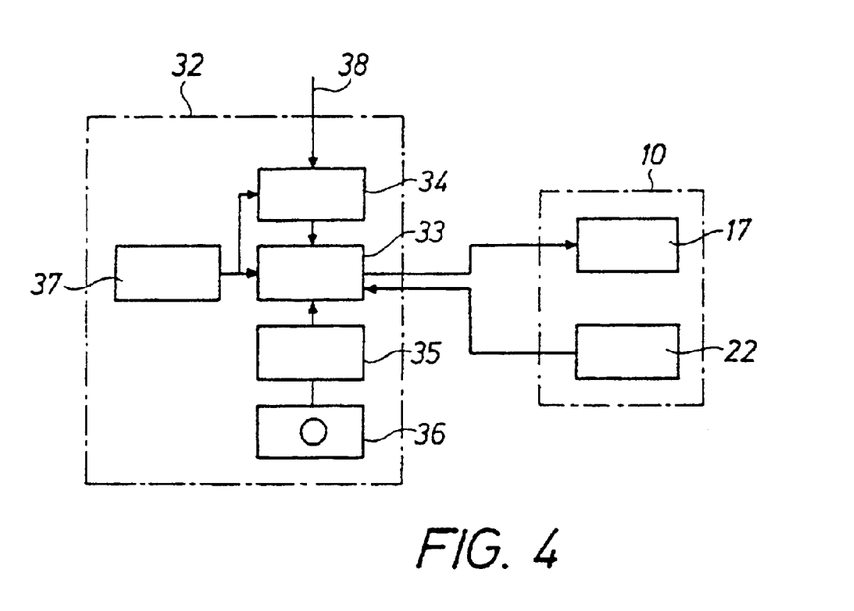
FIG. 4 is a block diagram showing the electrical system of the device of the invention.

When this procedure has been finished the person repeats the contraction of the pelvic floor muscles at intervals to exercise the muscles. The microprocessor 33 is programmed to compare the value represented by this signal with the maximum force value obtained and now stored in the memory 34 of unit 32, and to determine, if there is a predetermined relationship between the force values, e.g. if the force value represented by the signal transmitted from the probe 10 amounts to a predetermined percentage, e.g. at least 80%, of the force value in the memory and representing the maximum force initially applied by the person.

The microprocessor 33 should be programmed to switch on the power supply from the battery 37 to the motor 17 if the predetermined relationship prevails, in order to activate the vibrator in the probe so that the training is supplemented by vibratory therapy at a frequency in the range from 10 to 40 Hz, preferably in the range from 25 to 30 Hz. The vibration should be maintained for a predetermined period, e.g. 60 seconds, which can be set by means of the controller 36, and only as long as the muscle force does not decrease below the predetermined value thereof. When the period set has lapsed the person should continue the procedure by repeating the contraction at intervals of e.g. 60 seconds for a number of periods as prescribed by a physician or therapist. If the person even after rest periods is no longer able to apply the predetermined force the training should be terminated and should be resumed after a break of e.g. one or two days.

The training procedure should be repeated by the person periodically e.g. once every day or every week or several times each week, and as an initial step of each training pass the person registers the maximum contraction force that she is able to achieve. Hopefully, the strength of the pelvic floor muscles improves by repeated training, which is indicated by the force value to be stored in the unit being at a higher level each time a new training session is started. The person then has to apply a greater force by contraction of the pelvic floor muscles before the training is supplemented by vibration.

Although training by contraction of the pelvis floor muscles is known per se and training by vibration is also known per se in the field of rehabilitation of pelvic floor muscles the novelty of the invention is the combination of repeated contraction exercise and vibration under predetermined controlled conditions in order to improve the training.

Instead of transferring data from the probe to the processing unit by cable as described such transfer can be effected by telemetry which requires an analogue-to-frequency or analogue-to-digital converter, a transmitter and a battery to be part of the probe, which is possible.

Figure 5:
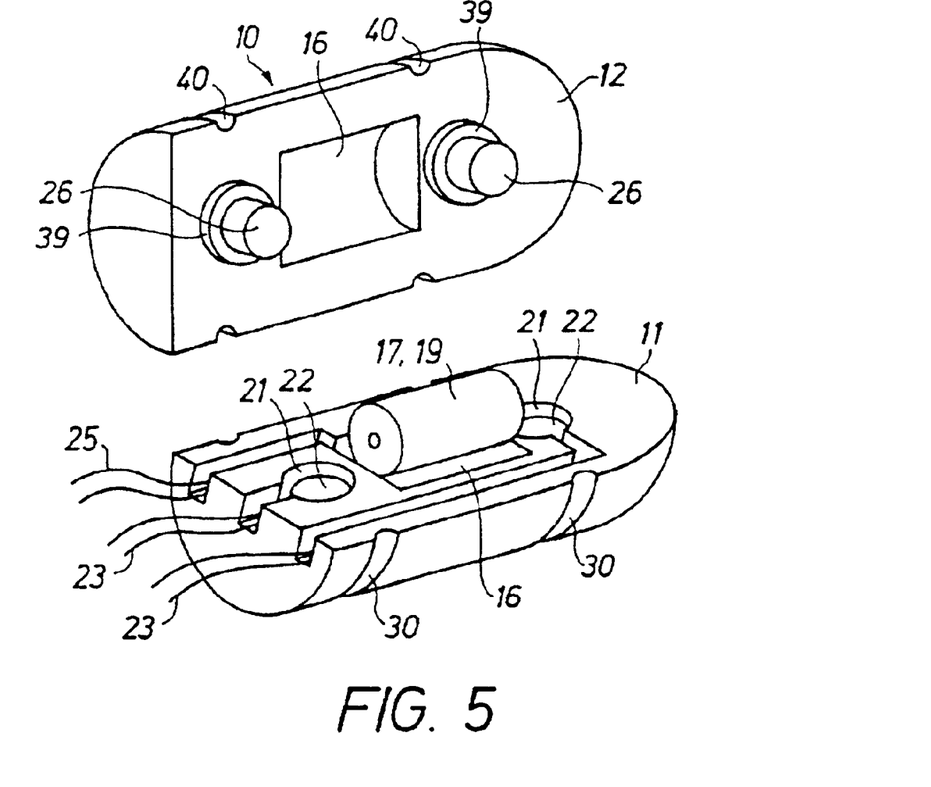
FIG. 5 is a perspective view of a second embodiment of the probe the two halves thereof being shown in a separated position.
Figure 6:
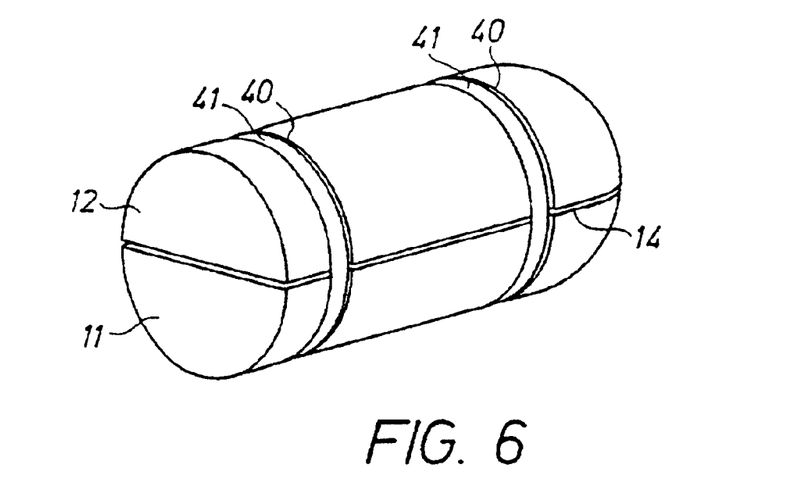
FIG. 6 is a perspective view of the probe in FIG. 5 when the two halves are closed.
Figure 7:
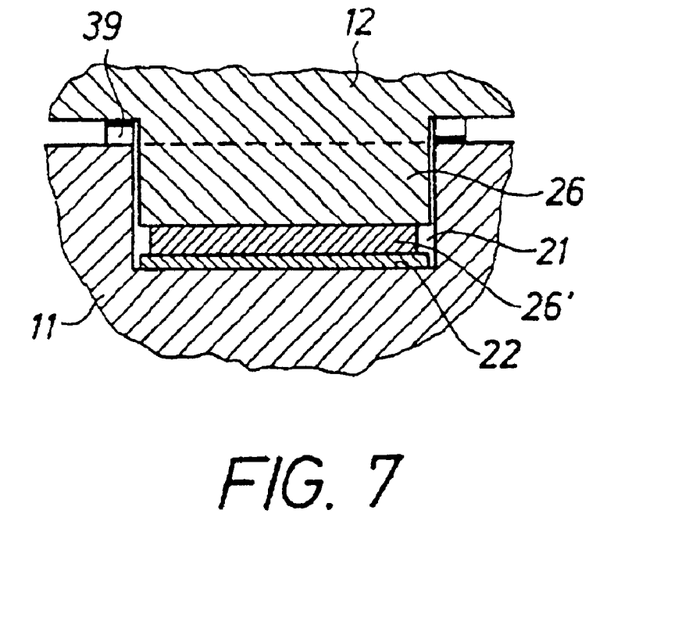
FIG. 7 is a fragmentary enlarged cross sectional view showing in more detail the sensor arrangement in the embodiment of FIGS. 5 and 6.

Referring to FIGS. 5 and 6 the probe disclosed therein comprises two halves 11 and 12 but they are not articulately interconnected as in the embodiment described above. An elastic ring 39 is passed onto each pin 26, and when the two halves of the probe are laid together the pins 26 are received in the recesses 21 to engage the force sensors 22 received therein, the two elastic rings 39 being interposed between the halves of the probe to maintain the gap 14 therebetween. The arrangement of the sensors is disclosed in more detail in FIG. 7. If the sensor 22 is a force sensitive resistor from International Electronics and Engineering, referred to above, a soft layer 26' should be disposed between the pin 26 and the sensor 22 which is supported by the rigid bottom of the recess 21. In FIG. 7 the ring 39 is shown as a corrugated ring but it can also comprise an elastic O-ring e.g. of rubber or similar elastic material. In the outside of the probe two circumferential grooves 40 are provided, and an elastic O-ring 41 or a resilient metal ring is received in each of the grooves to keep the probe halves together. When the probe inserted into the vagina or the rectum is exposed to force generated by contraction of the pelvic floor muscles, the probe halves will be pressed together under resilient compression of the elastic rings 39 a signal representing the force being transmitted by the force sensors 22 as in the first embodiment described above.

Figure 8:
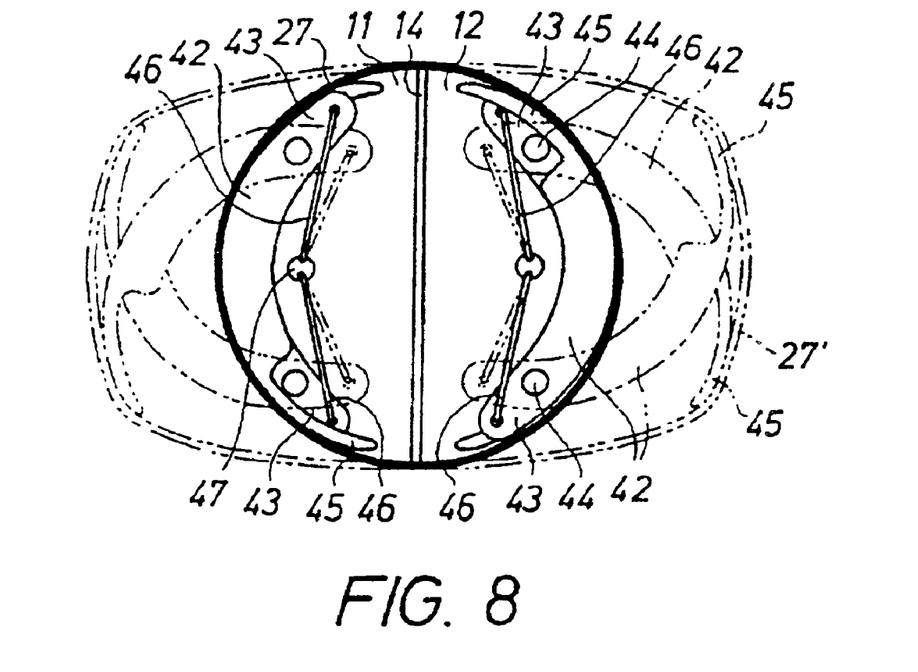
FIG. 8 is a cross sectional view of a modification of the embodiment in FIGS. 1 and 2 or in FIGS. 5 and 6.

In some cases it may be difficult for the training person to apply a contraction force on the probe because the tissue surrounding vagina is loose or because there is a substantial difference in size between the probe and the cavity in question. FIG. 8 discloses a modification of the first embodiment in FIGS. 1 and 2 or the second embodiment in FIGS. 5 and 6, which allows adjustment of the outside dimension of the probe. Each of the two halves 11 and 12 separated by the gap 14 and enclosed by the condom 27 of elastic material is provided with two double-armed levers which have arms 42 and 43 and are pivotally mounted on pins 44 extending axially of the probe. Each arm 42 has a flat end portion 45 which extends in the axial direction of the probe, and each arm 43 is connected to a wire or string 46 which is extended through a passage 47 in the associated half of the probe to the proximal end thereof. By pulling the wires or strings which can be effected by a suitable screw device to which the wires or strings are connected, the levers 42, 43 can be pivoted on the pins 44 to the position shown by dash lines, so that the flat end portions 45 expand the condom 27 e.g. to the position shown at 27' in FIG. 8. The wires or strings can be locked by suitable means with the levers in this position. In this manner the probe can be applied against the wall of the vagina for transmission of the contraction force applied by the training person, to the probe and thus to the sensors.

Figure 9:
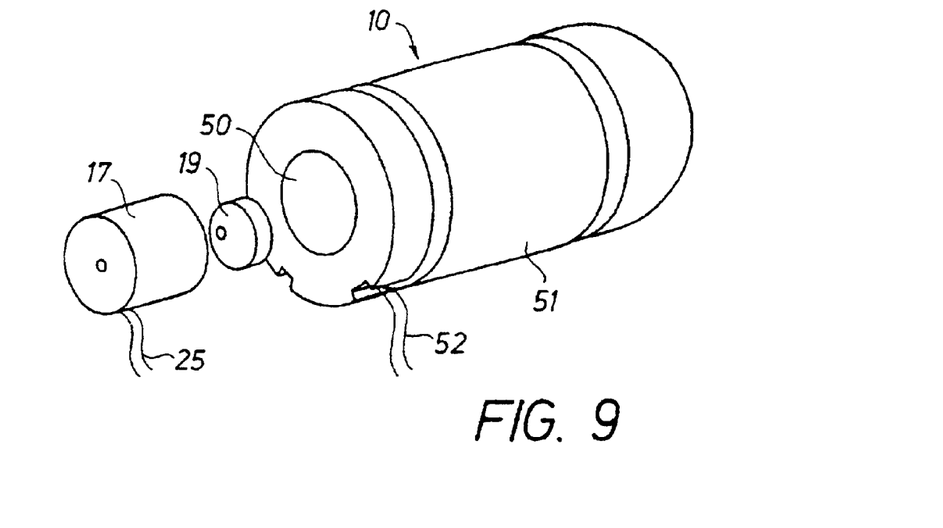
FIG. 9 is a perspective view of a fourth embodiment of the probe.

In the embodiment disclosed in FIG. 9 the probe 10 is formed by a unitary body having a central blind hole 50 into which the motor 17 with the unbalanced weight 19 is inserted although it is shown in FIG. 9 separated from the probe. In this case a single force sensor 51 is mounted on the outside of the probe. The sensor is wrapped around the probe and is fixed to the outside surface thereof, and it should be connected with the unit 32 by wires 52. In a modification individual sensors may be distributed circumferentially on the outside of the probe. It may be sufficient to provide two sensors only located diametrically opposite to each other.

The embodiments of the probe disclosed in FIGS. 5 and 6 and in FIG. 9, respectively, can be provided with a condom 27, and the mounting thereof at the proximal end of the probe can be as disclosed in FIG. 1.

Reference is now made to FIGS. 10 to 14 in the drawings. As in the embodiment of FIG. 1 the probe 10 comprises two halves 11 and 12 with a gap 14 therebetween and enclosed by a condom 27 which is clamped between a disk 28 and a plate 29 by means of screws 30. The plate 29 can be shaped as shown in FIG. 2.

Figure 10:
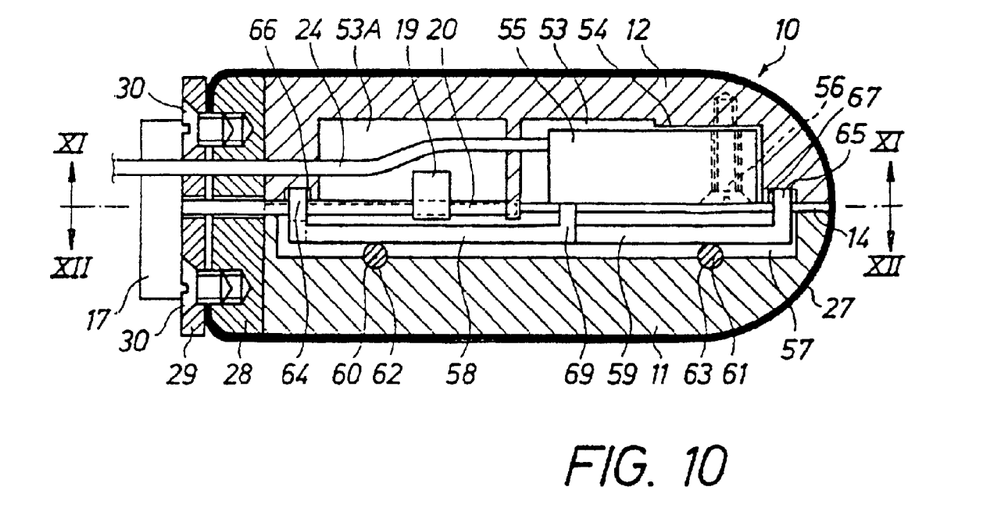
FIG. 10 is an axial cross sectional view of the probe in a fifth embodiment thereof.

In the upper half 12 as seen in FIG. 10 there is formed a cavity 53 with a flat bottom surface which has a raised portion 54, and a hermetically sealed force sensor 55 such as a wire strain gauge is engaged with the surface of the raised portion 54 and is attached to it by means of screws 56 screwed into threaded blind holes in the half 12. The sensor extends into the deeper part of the cavity 53 the bounding surfaces of which surround the sensor leaving a free space between the sensor and the surfaces.

Figure 11:
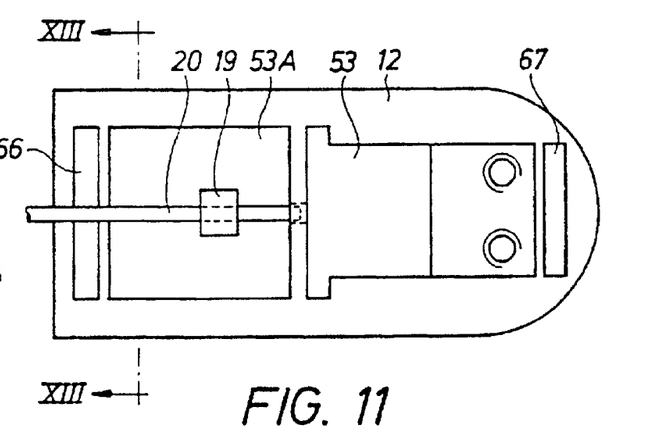
FIG. 11 is a plan view of the bottom side of the upper element of the probe in FIG. 10.
Figures 12, 14:
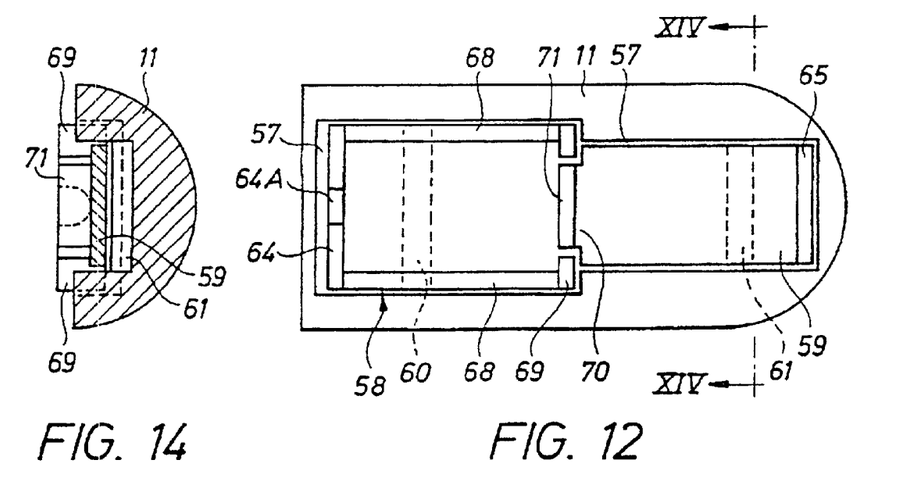
FIG. 12 is a plan view of the lower element of the probe in FIG. 10 with the lever system mounted therein.
FIG. 14 is a cross sectional view taken along line XIV—XIV in FIG. 12.
Figure 13:
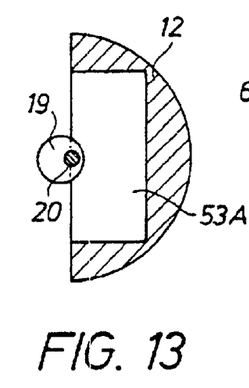
FIG. 13 is a cross sectional view taken along line XIII—XIII in FIG. 11.

A rectangular cavity 57 with flat bottom surface is formed in the lower half 11 of the probe. Two metal sheet double-armed levers 58 and 59 are pivotally supported in the cavity by means of transverse cylindrical rods 60 and 61 received by grooves 62 and 63 in the bottom of the cavity 57. Rods 60 and 61 can be replaced by sharp edges integral with the lower half 11 and protruding from the flat bottom surface of cavity 57. Each of the levers 58 and 59 forms at one end thereof a flange 64 and 65, respectively, projecting perpendicularly upwards from the respective lever, said flange being received by a rectangular cavity 66 and 67, respectively, in the upper half 12 of the probe 10. Lever 58 is U-shaped and forms two limbs 68 projecting from flange 64, which at the end opposite to flange 64 each have a flange 69 projecting perpendicularly upwards from the limbs. The other end of the lever 59 opposite to flange 65 forms a central tongue 70 with a flange 71 projecting perpendicularly upwards from the tongue which is received between the limbs 68. The flanges 69 and 71 abut the sensor 55 at the lower side thereof at the end of the sensor which is opposite to the end where the sensor is attached to the upper half 12.

A cavity 53A in the upper half 12 forms together with cavity 57 in the lower half 11 a hollow space in the probe which houses the vibrator comprising the unbalanced weight 19 on the drive shaft 20. As in the embodiment of FIG. 1 also the drive motor of the vibrator can be mounted inside the probe but in the embodiment of FIG. 10 the shaft 20 is rotatably mounted in the upper half 12 and extends to the motor 17 which is located on the outside of the probe and is mounted to plate 29. A notch 64A is provided in flange 64 for the passage of the shaft.

When the probe is inserted into vagina as shown in FIG. 3 the training procedure as described above is performed. Passive and active forces applied to the probe during resting and muscle contraction, respectively, anywhere along the longitudinal axis of the probe are summarized by the levers 58 and 59 and transferred to the sensor 55, which measures the resultant force on a transverse axis and converts this force into an electric output signal which will be independent of the position of the force attack on the longitudinal axis of the probe. The probe allows measurement under all normal conditions e.g. when the patient is sitting, standing, or lying down, and is insensitive to intra-abdominal pressure.

The output signal from the sensor 55 is transferred by means of cable 24 to an external electronic processing unit, preferably a hand held, battery operated unit such as unit 32 described with reference to FIG. 4.

The processing unit receives the output signal from the sensor 55 and processes this signal in order to present and store the result of every single muscle contraction as well as the date and time thereof. This operation serves two purposes:

1. Diagnostics. The function of the pelvic floor muscles can be tested and the data obtained can be stored for future analysis.

2. Selftraining. The patient can use the processing unit for training the pelvic floor muscles. Prior to each training session the patient performs a test which will form the basis for biofeedback. For optimal training effect the patient is informed, instantly after each muscle contraction about the quality of the work performed. Thus, the individual patient properties determine the intensity and number of contractions as well as the duration and repetition of vibration periods. The processing unit can indicate for the patient when the optimal number of contractions is reached, muscle fatigue thus being taken into consideration.

In females with stress urinary incontinence (SUI) the following factors seem to be related to the development of the disease: obesity, more than three vaginal deliveries, and birth weights over 4 kg. Moreover, studies have shown that a reduced force generating capacity of the pelvic floor musculature is related to the development of SUI. Using a recently developed method it has been shown that the rise force development (RFD), i.e. how rapidly the force change takes place (N/s), is significantly reduced in females with SUI.

A reduced RFD may occur due to several possibilities:
i) The internal force-velocity relationship/capacity of the muscle fibers is reduced;
ii) the length of the muscles and their connective tissue is increased so that more time is needed to 'take up the slack' within the tissue;
iii) the attachment of the muscle fibers to the connective tissue is disrupted so that no increase in tension occurs; and
iv) the nervous system is not appropriately trained to send impulses with high enough frequency.

Muscular tissues respond specifically to the training imposed on the tissue. Therefore, it is important that different physiological properties of the pelvic floor are specifically trained. The described device can give information to the patient on several parameters, e.g. two different force parameters, viz. developed force (N) and raise force development RFD (N/s). Therefore, depending on the results of the examination making use of the device of the invention, the physician/gynecologist is able to decide whether 'force feedback', 'RFD feedback' or a mixture of both, should be used by the patients. Prior art test/training devices could not take these new parameters into consideration due to insufficiency in the construction thereof, nor could they measure them. It is important to note that said two parameters are different in accordance with the force-velocity relationship discovered by Hill in 1938:

a high force may be developed despite a low velocity, and
a high RFD does not necessarily coincide with a high force development.

After a predetermined training period the processing unit can be taken to a doctor for analysis, the data stored in the processing unit being transferred to and stored in a PC for analysis and presentation of the result, numerically or graphically, as well as print out thereof.

Instead of transferring data from the probe to the processing unit by cable such transfer can be effected by telemetry, which gives a greater freedom for the patient because the cable can be dispensed with. Telemetry requires an analogue-to-frequency or analogue-to-digital converter, a transmitter and a battery to be part of the sensor, which is possible.

When the device is used in rectum in order to indicate fecal incontinence the result thereof can be used to diagnose spinal deficiencies.

What is claimed is:

1. A method for training floor muscles in order to treat or prevent urinary or faecal incontinence comprising the steps of
   (a) inserting a probe with a vibrator and a force sensor into a person's vagina or rectum,
   (b) ascertaining initially the highest value of a force that can be applied by the person at contraction of the pelvic floor muscles with vibrator operating or shut off,
   (c) registering said highest value, repeating the contraction of the pelvic floor muscles at intervals and comparing the force applied by the pelvic floor muscles at each contraction with the highest value,
   (d) activating the vibrator if by comparison the force applied by the person at each contraction of the pelvic floor muscles has a predetermined relationship to said registered highest value, and
   (e) maintaining the vibrator activated for a predetermined period as long as the predetermined relationship is maintained.

2. The method of claim 1, wherein the vibrator is shut off when performing step (b).

3. The method of claim 1, wherein the vibrator is kept operating when performing step (b).

4. The method of claim 1 wherein said predetermined relationship is defined as a predetermined percentage of the registered highest value.

5. The method of claim 4 wherein said percentage is about 80%.

6. The method of claim 1 wherein the frequency of the vibrator ranges from 10 to 40 Hz.

7. The method of claim 6 wherein the frequency of the vibrator ranges from 25 to 30 Hz.

8. A device for training pelvic floor muscles on order to treat or prevent urinary or faecal incontinence comprising a probe adapted to be inserted into a vagina or rectum and having at least one sensor for dynamically ascertaining a force transferred to the probe by contraction of the pelvic floor muscles with a vibrator operating or shut off in the probe, and a microprocessor operatively connected with said at least one sensor and the vibrator wherein the vibrator is energized only at a value related to a predetermined value of said force, as ascertained by the said sensor.

9. The device of claim 8 wherein the probe comprises a first and a second element mutually spaced by an axial gap therebetween, the sensor being provided for sensing dynamically passive and active forces transferred to the probe by the pelvic floor muscles and acting on said first and second elements over said gap in the transverse direction of the probe, and for converting said force to an electric output signal.

10. The device of claim 9 comprising a single sensor located in said first element, and a lever system in said second element for transferring to the sensor from axially spaced positions of the probe said dynamically passive and active forces, and for applying said forces to the sensor.

11. The device of claim 10 wherein two aligned double-armed levers are pivotally mounted between the ends thereof in said second element, and wherein each lever has one end engaging said first element at said positions spaced axially of the probe, and the other end operatively connected to the sensor.

12. The device of claim 8 comprising a support plate on the proximal end of said probe to be engaged with the body at the opening of vagina or rectum, respectively.

13. The device of claim 8 comprising a portable hand-held unit including the microprocessor, a memory for registering a predetermined force value, and means for connecting the microprocessor to the vibrator and said at least one sensor for comparing the value of the force ascertained by the sensor with said predetermined force value, and for activating the vibrator in dependence of the result of the comparison.

14. The device of claim 13 wherein said comparison includes a predetermined relationship between said predetermined force value and the value of the force ascertained by said at least one sensor.

15. The device of claim 14 wherein said relationship defines the value of the force ascertained by said at least one sensor as a predetermined percentage of said predetermined value of said force.

16. The device of any of claims 8 to 15 wherein said at least one sensor comprises an electronic force-sensing device.

17. The device of claim 9 wherein said first and second elements are separated by at least one elastic element.

18. The device of claim 9 wherein means are provided for adjusting the outside cross dimension of the probe.

19. The device of claim 8, wherein said at least one sensor is located on the outside surface of the probe.

* * * * *